(12) United States Patent
Wang et al.

(10) Patent No.: US 12,415,893 B2
(45) Date of Patent: Sep. 16, 2025

(54) ANHYDRIDE COMPOUND, POLYIMIDE, AND THIN FILM

(71) Applicant: INDUSTRIAL TECHNOLOGY RESEARCH INSTITUTE, Hsinchu (TW)

(72) Inventors: Yi-Syuan Wang, Taoyuan (TW); Jeng-Yu Tsai, Chiayi (TW); Chi-En Kuan, Zhudong Township (TW); Jyh-Long Jeng, New Taipei (TW); Chih-Ming Hu, Hsinchu (TW); Chen-Hsi Cheng, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 636 days.

(21) Appl. No.: 17/888,269

(22) Filed: Aug. 15, 2022

(65) Prior Publication Data

US 2023/0101144 A1      Mar. 30, 2023

Related U.S. Application Data

(60) Provisional application No. 63/240,584, filed on Sep. 3, 2021.

(30) Foreign Application Priority Data

Dec. 7, 2021    (TW) ................. 110145616

(51) Int. Cl.
C08G 73/10      (2006.01)
C07D 307/89    (2006.01)
C08J 5/18          (2006.01)

(52) U.S. Cl.
CPC ....... C08G 73/1071 (2013.01); C07D 307/89 (2013.01); C08G 73/1028 (2013.01); C08J 5/18 (2013.01); C08J 2379/08 (2013.01)

(58) Field of Classification Search
None
See application file for complete search history.

(56) References Cited

U.S. PATENT DOCUMENTS 5,047,560 A    9/1991  Shoji et al.
5,188,903 A    2/1993  Liao et al.
(Continued)

FOREIGN PATENT DOCUMENTS

CN    103102794 A    5/2013
CN    107022075 A    8/2017
(Continued)

OTHER PUBLICATIONS

Chinese Office Action and Search Report for Chinese Application No. 202210253455.9, dated Nov. 29, 2023.
(Continued)

Primary Examiner — Megan McCulley
(74) Attorney, Agent, or Firm — Birch, Stewart, Kolasch & Birch, LLP

(57) ABSTRACT

An anhydride compound, polyimide, and thin film are provided. The anhydride compound has a chemical structure of

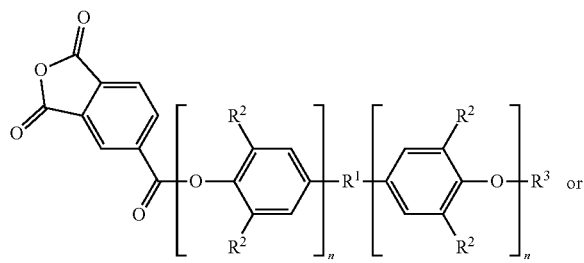

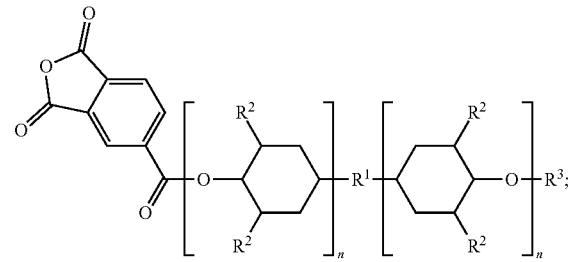

wherein $R^1$ is

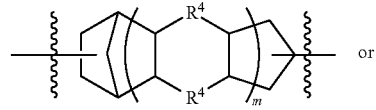

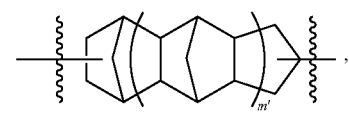

(Continued)

each of $R^4$ is independently $C_{1-6}$ alkylene group, m is an integer of 0 to 10, and m' is an integer of 1 to 10; n is an integer of 1 to 10, each of $R^2$ is independently hydrogen, saturated or unsaturated $C_{1-6}$ hydrocarbon group, $CF_3$, silanol group, silyl group, or $Al(OH)_3$; and $R^3$ is

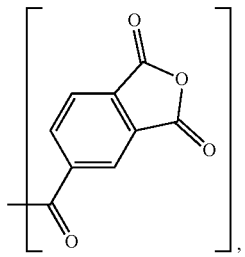

silanol group, silyl group, or $Al(OH)_3$. The anhydride compound can be reacted with a diamine compound to form a polyimide.

9 Claims, No Drawings

(56) References Cited

U.S. PATENT DOCUMENTS

| 7,655,278 | B2 | 2/2010 | Braidwood et al. |
| 8,053,077 | B2 | 11/2011 | Braidwood et al. |
| 2005/0165202 | A1 | 7/2005 | Nakamura et al. |
| 2017/0009017 | A1 | 1/2017 | Huang et al. |
| 2019/0367647 | A1* | 12/2019 | Li ............ C09D 133/14 |
| 2020/0263052 | A1 | 8/2020 | Peters et al. |

FOREIGN PATENT DOCUMENTS

| CN | 105683285 A | 6/2018 |
| CN | 109312071 A | 2/2019 |
| CN | 109970519 A | 7/2019 |
| TW | 201531502 A | 8/2015 |
| TW | 202012498 A | 4/2020 |
| WO | WO 2021/117586 A1 | 6/2021 |

OTHER PUBLICATIONS

Ho et al., "Thermal degradation kinetics and flame retardancy of phosphorus-containing dicyclopentadiene epoxy resins", Polymer Degradation and Stability, vol. 91, Issue 10, Oct. 2006, pp. 2347-2356.

TW Office Action was issued on Jun. 9, 2022 for the corresponding application No. 110145616 in Taiwan.

* cited by examiner

ANHYDRIDE COMPOUND, POLYIMIDE, AND THIN FILM

CROSS REFERENCE TO RELATED APPLICATIONS

This application claims the benefit of U.S. Provisional Application No. 63/240,584, filed on Sep. 3, 2021, the entirety of which is incorporated by reference herein.

The present application is based on, and claims priority from, Taiwan Application Serial Number 110145616, filed on Dec. 7, 2021, the disclosure of which is hereby incorporated by reference herein in its entirety.

TECHNICAL FIELD

The technical field relates to anhydride compounds.

BACKGROUND

Networks are gaining increasing popularity, and consumers are demanding high-quality communication at higher-speeds and lower latency. In response to the 5G era, which promises wider network coverage and faster transmission rates, the use of soft-board materials demands low transmission loss (Dielectric Loss, or Df) and low dielectric coefficients (Dielectric Constant, or Dk) be greatly increased. Using polyimide (PI) as an example, the board material of a conventional polyimide (PI) film cannot satisfy the requirements for high frequencies and high speeds. As such, the modified PI (MPI) for 5G high frequency and high speed applications means that the product is attracting much attention in this industry.

Accordingly, development of a novel synthesis raw material for the board material is called-for to satisfy the above requirements.

SUMMARY

One embodiment of the disclosure provides an anhydride compound, having a chemical structure of

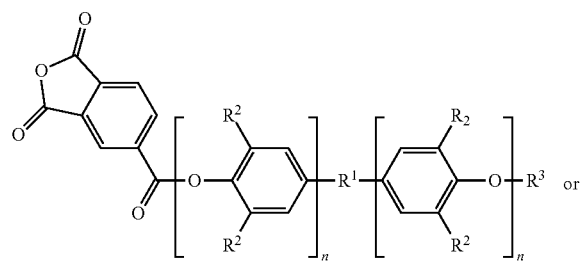

or

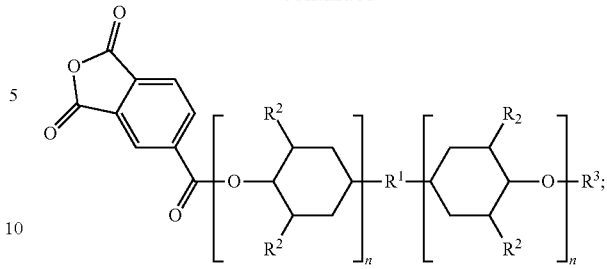

wherein $R^1$ is

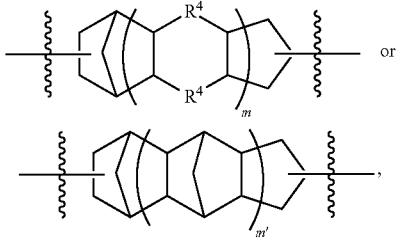

or each of $R^4$ is independently $C_{1-6}$ alkylene group, m is an integer of 0 to 10, and m' is an integer of 1 to 10; n is an integer of 1 to 10; each of $R^2$ is independently hydrogen, saturated or unsaturated $C_{1-6}$ hydrocarbon group, $CF_3$, silanol group, silyl group, or $Al(OH)_3$; and $R^3$ is

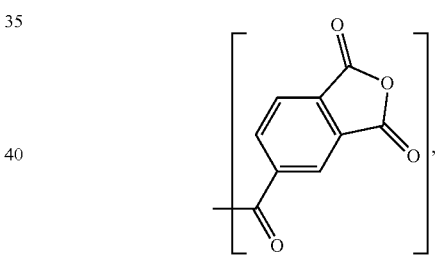

silanol group, silyl group, or $Al(OH)_3$.

One embodiment of the disclosure provides a polyimide, being formed by reacting an anhydride compound and a diamine compound; wherein the anhydride compound has a chemical structure of

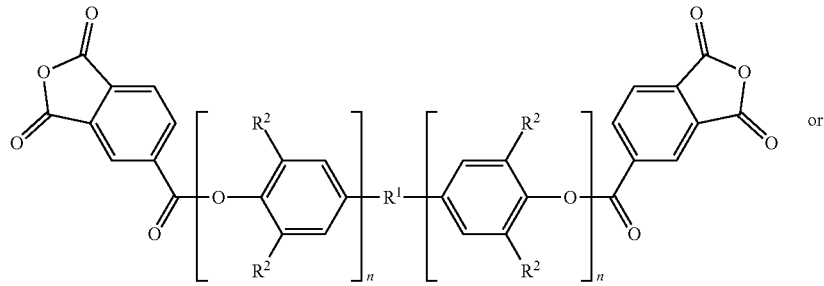

or

-continued

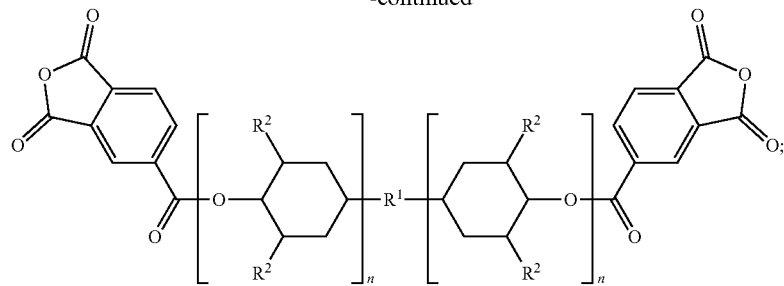

wherein R¹ is

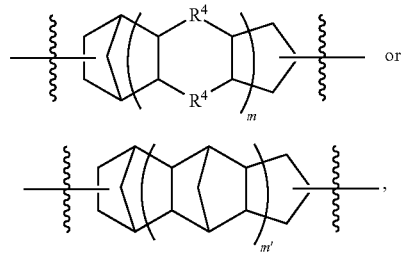

each of R⁴ is independently $C_{1-6}$ alkylene group, m is an integer of 0 to 10, and m' is an integer of 1 to 10; n is an integer of 1 to 10; and each of R² is independently hydrogen, saturated or unsaturated $C_{1-6}$ hydrocarbon group, $CF_3$, silanol group, silyl group, or $Al(OH)_3$.

One embodiment of the disclosure provides a thin film, including the described polyimide, wherein the thin film has a thickness of 10 μm to 75 μm, and a dielectric constant of 2.5 to 3 at 10 GHz.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

One embodiment of the disclosure provides an anhydride compound, having a chemical structure of

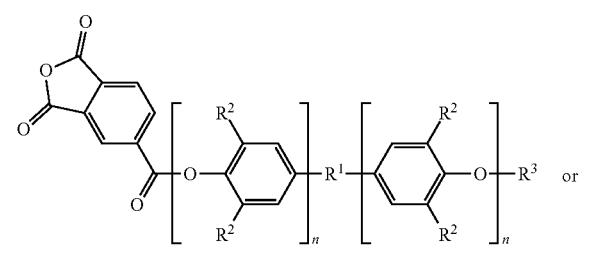 or

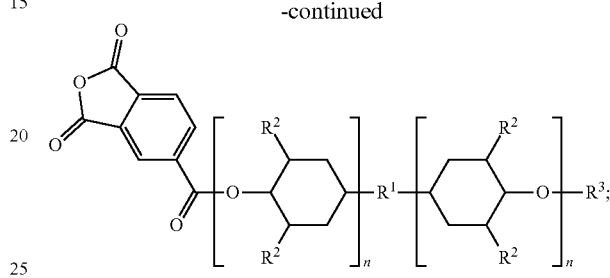

wherein R¹ is

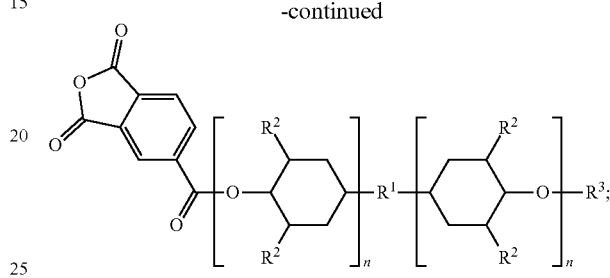

each of R⁴ is independently $C_{1-6}$ alkylene group, m is an integer of 0 to 10, and m' is an integer of 1 to 10; n is an integer of 1 to 10; each of R² is independently hydrogen, saturated or unsaturated $C_{1-6}$ hydrocarbon group, $CF_3$, silanol group, silyl group, or $Al(OH)_3$; and R³ is

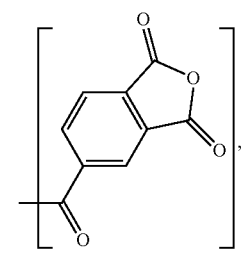

silanol group, silyl group, or $Al(OH)_3$. The anhydride compound can be synthesized in the following steps:

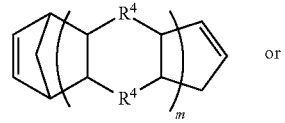 or

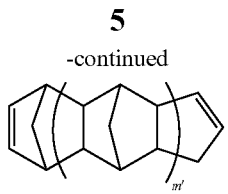

can react with

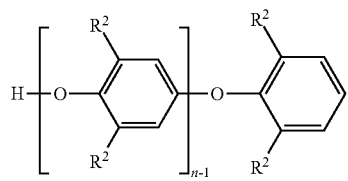

in the presence of acidic catalyst (e.g. AlCl₃, HF, or another acidic catalyst) to form a diol compound, as shown in below formula.

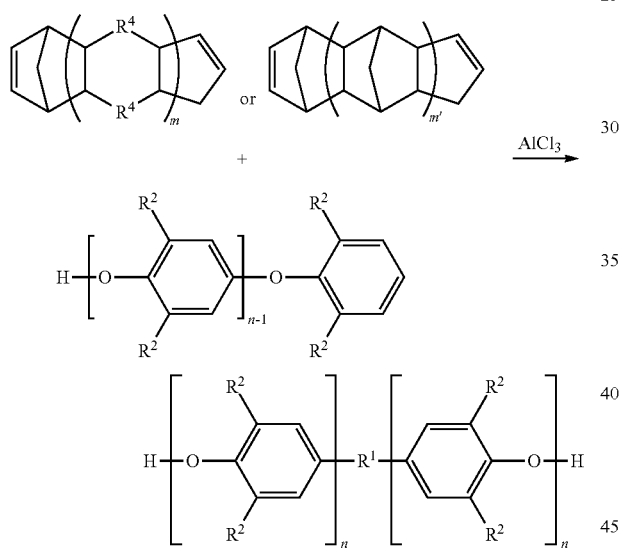

Subsequently, benzyl bromide (BnBr), chloromethyl methyl ether (MeOCH₂Cl), tert-butyldimethylsilyl ether (TBSCl), methanesulfonyl chloride (MsCl), or dimethyl sulfate is used to protect one alcohol group on one side of the diol compound. Take MsCl as an example, the reaction is shown as below formula.

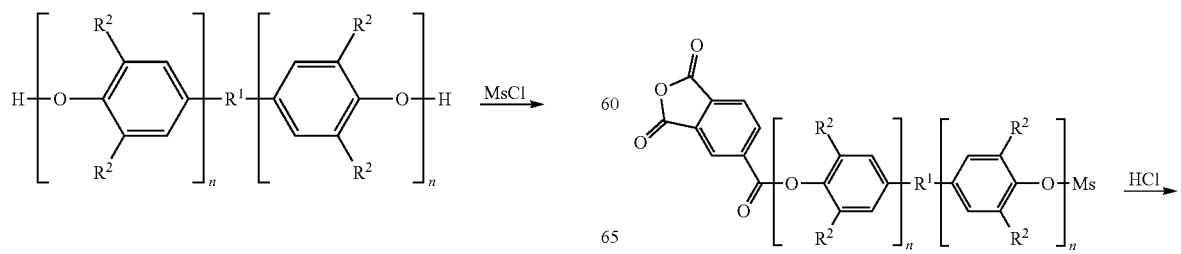

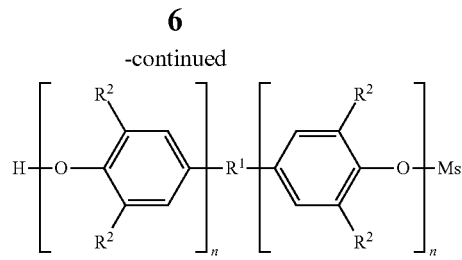

Subsequently, the compound containing the protection group can react with trimellitic anhydride chloride (TMAC) to form an anhydride compound, as shown in below formula.

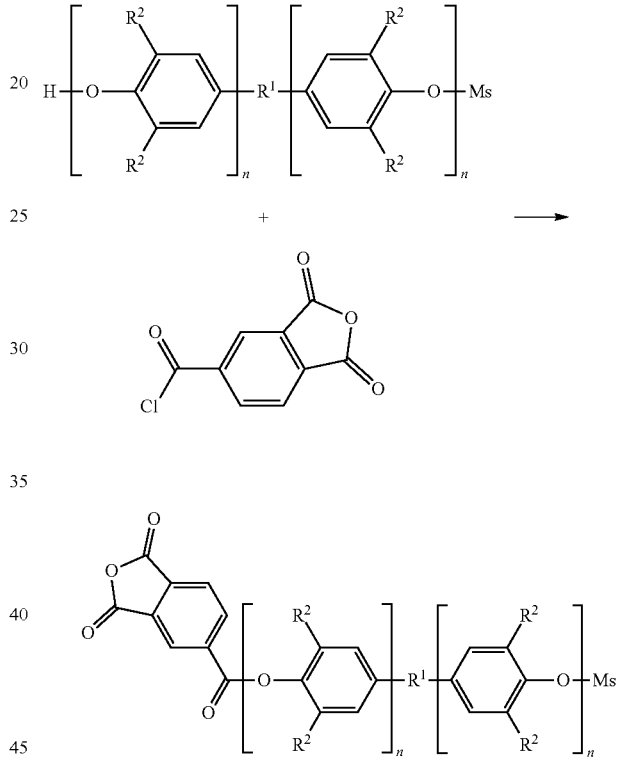

Subsequently, a de-protection reaction is performed, as shown in below formula. The de-protection reagent can be HCl, I₂, F⁻, LDA (lithium diisopropylamide), BBr₃, or another suitable reagent.

-continued

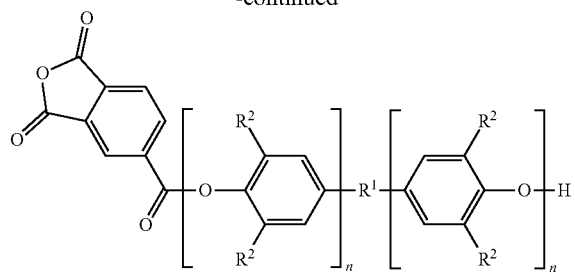

Subsequently, R³—Cl can be added to perform a substitution reaction to form an anhydride compound, as shown in below formula.

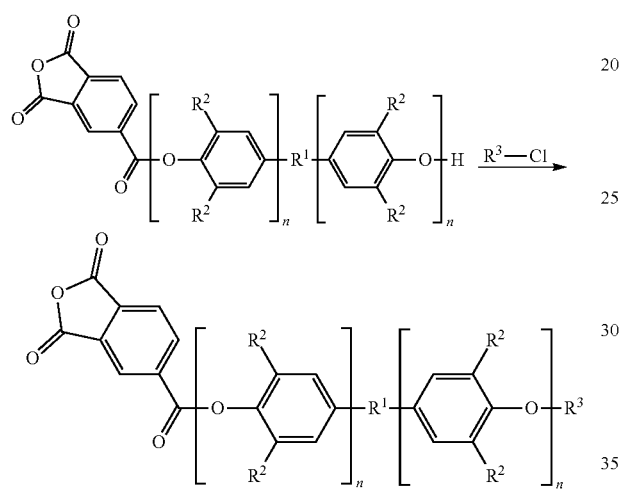

In some embodiments, the anhydride compound formed by the above reactions may have a chemical structure of

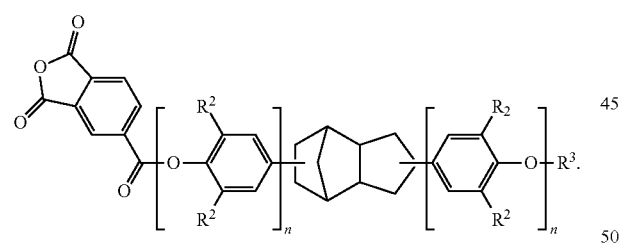

Alternatively, the diol compound can directly react with TMAC to form an anhydride compound, as shown in below formula.

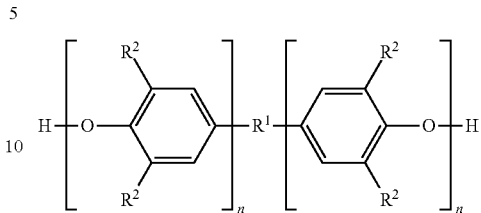

In some embodiments, the anhydride compound formed by the above reactions may have a chemical structure of

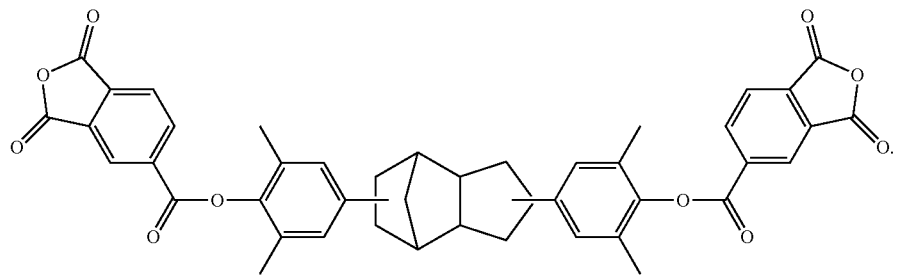

In some embodiments, the diol compound can be firstly hydrogenated. BnBr, MeOCH$_2$Cl, TBSCl, MsCl, or dimethyl sulfate is then used to protect one alcohol group on one side of the diol compound. Take MSCl as an example, and the reaction is shown as below formula.

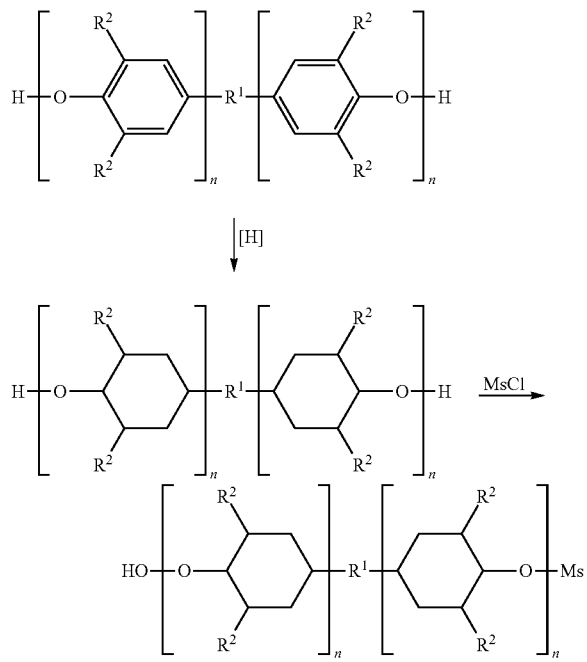

Subsequently, the compound containing the protection group can react with TMAC to form an anhydride compound, as shown in below formula.

Subsequently, a de-protection reaction is performed, as shown in below formula. The de-protection reagent can be HCl, I$_2$, F$^-$, LDA, BBr$_3$, or another suitable reagent.

Subsequently, R$^3$—Cl can be added to perform a substitution reaction to form an anhydride compound, as shown in below formula.

In some embodiments, the anhydride compound formed by the above reactions may have a chemical structure of On the other hand, the diol compound can firstly undergo hydrogenation, and then react with TMAC to form the anhydride compound, as shown in below formula.

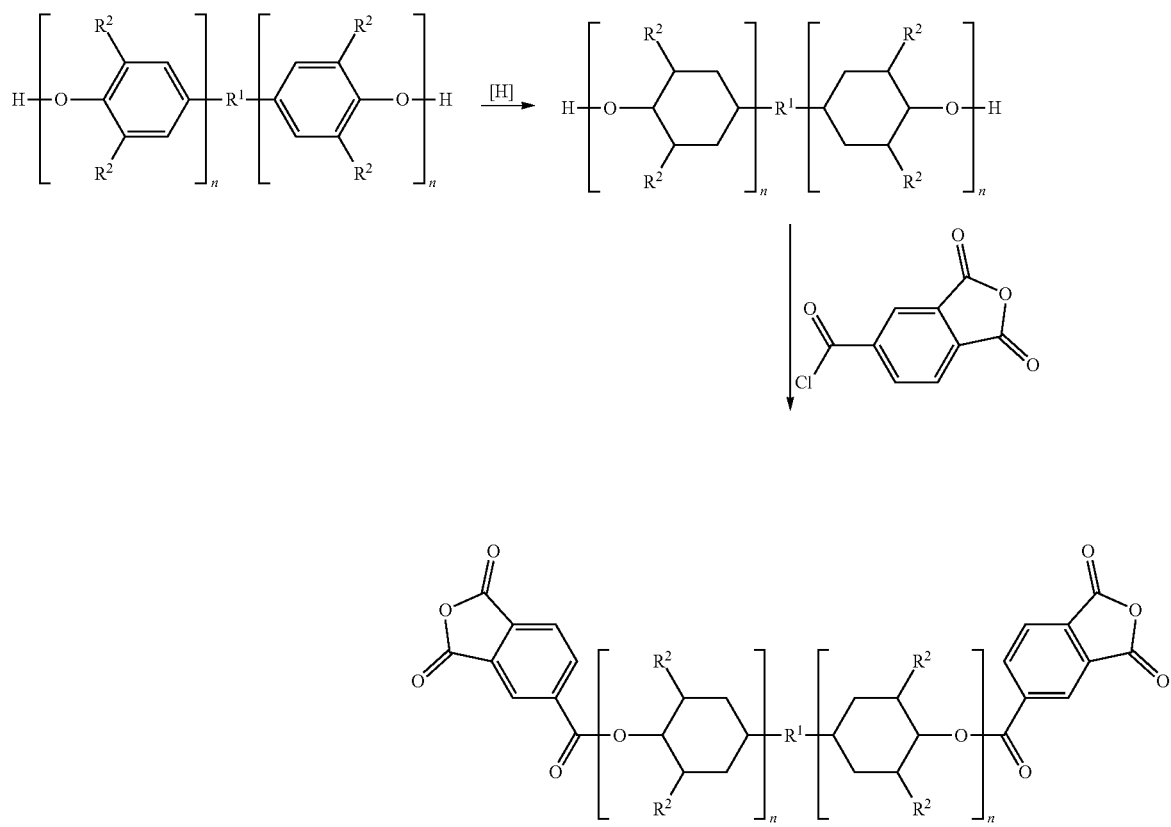

In some embodiments, the anhydride compound formed by the above reactions may have a chemical structure of

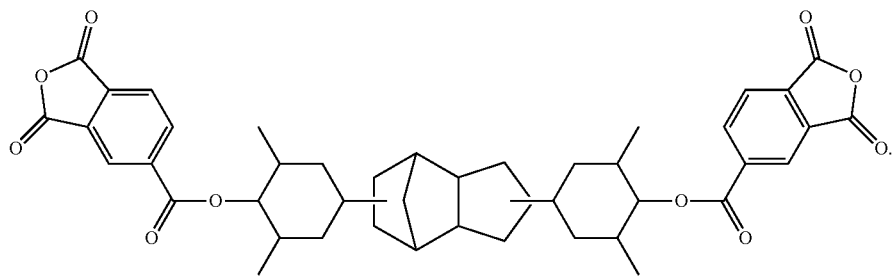

It should be understood that the above reactions are only for illustrating a possible synthesis path of the anhydride compound, which is not the only applicable synthesis path. One skilled in the art may adopt any applicable synthesis path according to his/her requirements for forming the anhydride compound in the disclosure.

One embodiment of the disclosure provides a polyimide formed by reacting the described anhydride compound with a diamine compound. Take dianhydride compound as an example, the reaction is shown below:

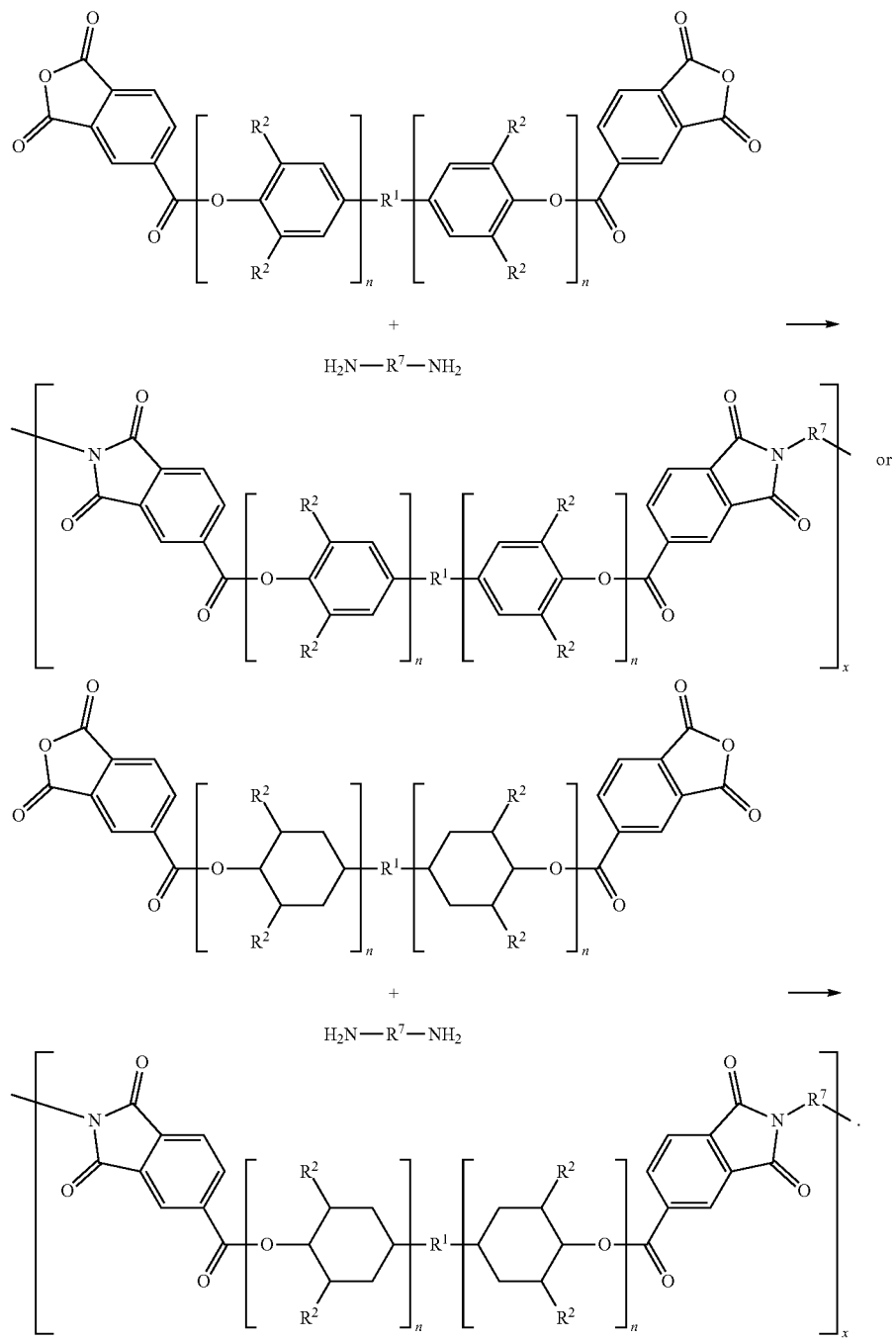

In the above formula, $R^7$ correspond to the diamine compound type, as described below. x is the repeating number of the repeating unit in the polyimide, which is related to the molecular weight of the polyimide.

In some embodiments, the diamine compound has a chemical structure of

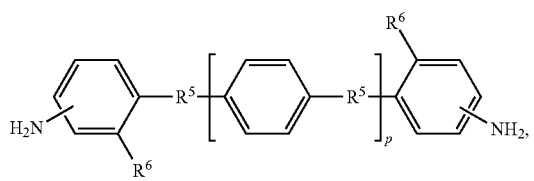

wherein p is an integer of 0 to 5; each of $R^5$ is independently —O—, —NH—, $C_{1-4}$ alkylene group, —$SO_2$—, —$CF_2$—, —$C_2F_4$—, —(C=O)O—, —O(C=O)—, —(C=O)NH—, or —NH(C=O)—; and each of $R^6$ is independently H, $CH_3$, or $CF_3$. For example, the diamine compound can be 4,4'-oxydianiline (ODA), which has a chemical structure of

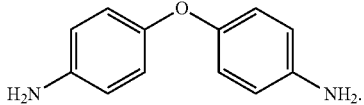

In some embodiments, the diamine compound can be 4-aminobenzoic acid 4-aminophenyl ester, which has a chemical structure of

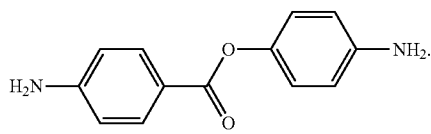 [SMILES: Nc1ccc(OC(=O)c2ccc(N)cc2)cc1]

In some embodiments, the diamine compound can be 1,4-bis(4-aminophenoxy)benzene, which has a chemical structure of

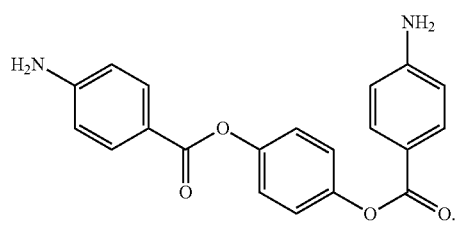 [SMILES: Nc1ccc(C(=O)Oc2ccc(OC(=O)c3ccc(N)cc3)cc2)cc1]

In some embodiments, the diamine compound can be 1,4-benzenedicarboxylic acid bis(4-aminophenyl) ester, which has a chemical structure of

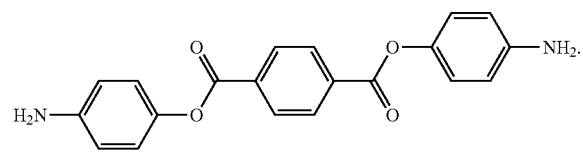 [SMILES: Nc1ccc(OC(=O)c2ccc(C(=O)Oc3ccc(N)cc3)cc2)cc1]

In some embodiments, the diamine compound can be 4,4'-(4,4'-isopropylidene diphenyl-1,1'-diyldioxy)dianiline, which has a chemical structure of

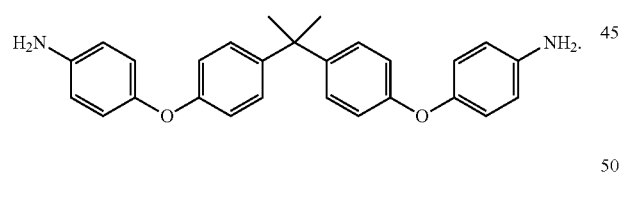

One embodiment of the disclosure provides a thin film, including the described polyimide. The thin film has a thickness of 10 μm to 75 μm, and a dielectric constant of 2.5 to 3 at 10 GHz. The dielectric constant of the polyimide thin film is related to the thickness of the polyimide thin film. If the dielectric constant of the polyimide thin film at 10 GHz is too high, the polyimide thin film cannot meet the requirements for its application as 5G board material.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity.

EXAMPLES

In the following Examples, the dielectric constant of the thin film at 10 GHz was measured by the standard JISC2565, the dielectric loss of the thin film at 10 GHz was measured by the standard JISC2565, and the moisture absorption of the thin film was measured by the standard means of the follows. First, the film was heated in an oven to 105° C. for 30 mins, then moved to a drying box for cooling down and the weight of the film ($W_0$) was recorded. Next, the film was soaked in D. I. water for 24 hours and the weight after water absorption ($W_1$) was recorded. The moisture absorption of the thin film is ($W_1-W_0$)/$W_0 \times 100\%$.

Example 1

$AlCl_3$ (0.10 mole, 13.11 g) serving as an acidic catalyst was added to and dissolved in 2,6-dimethylphenol (DMP, 1.18 mol, 144.15 g) solution, and dicyclopentadiene (DCPD, 0.60 mol, 78.00 g) was then added, and heated to react. After reaction, the solution was allowed to cool down to room temperature, and potassium hydroxide solution (5 wt %, 0.06 mol) was added to the reaction result to neutralize it. The diol compound was then extracted with toluene. The above reaction is shown below:

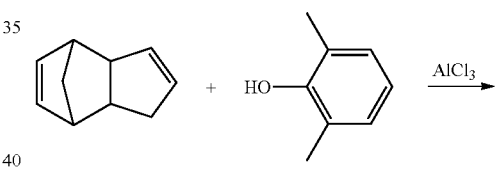

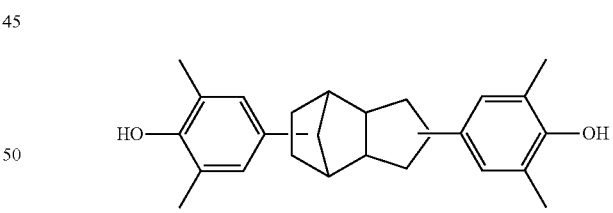

Pyridine (0.13 mol, 13.11 g) was added to trimellitic anhydride chloride (TMAC, 0.33 mol, 70.00 g) solution, which was then dropwise added to the diol compound solution to react for 24 hours. Afterward, the solvent of the reaction result was removed, and the reaction result was further dried in an oven to obtain an anhydride compound. The $^1$H NMR spectrum of the anhydride compound is shown below: $^1$H NMR (400 MHz, $CDCl_3$): δ 2.14 (s, 4H, aliphatic), 2.19 (s, 9H, aliphatic), 2.31 (s, 2H, aliphatic bridge), 7.14 (s, 4H, —Ar), 8.23 (d, 2H, phthalic anhydride, J=7.88 Hz), 8.76 (d, 2H, phthalic anhydride, J=7.88 Hz), 8.88 (s, 2H, phthalic anhydride). The reaction is shown below:

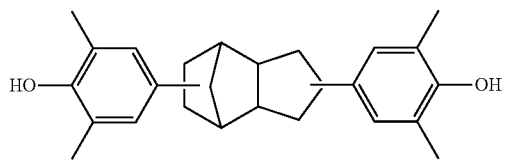

+

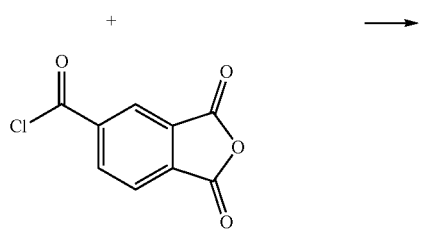

→

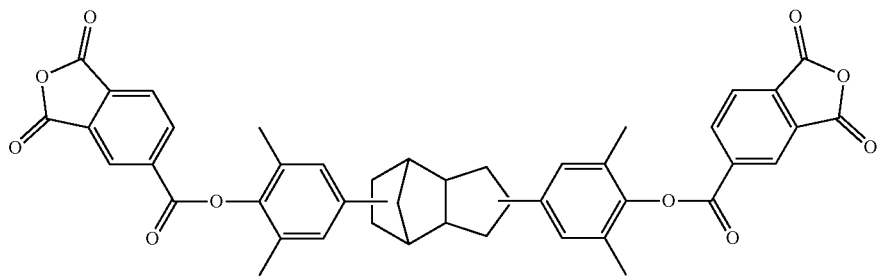

The anhydride compound and ODA were allowed to react at 25° C. for 6 hours to form polyimide. The polyimide solution was coated to form a thin film having a thickness of about 50 μm for measuring its dielectric constant at 10 GHz (2.80), dielectric loss at 10 GHz (0.006), and moisture absorption (0.5%).

Comparative Example 1 p-Phenylenebis(trimellitate anhydride) (TAHQ) and ODA were allowed to react at 25° C. for 6 hours to form polyimide. The polyimide solution was coated to form a thin film having a thickness of about 50 μm for measuring its dielectric constant at 10 GHz (3.5), dielectric loss at 10 GHz (0.007), and moisture absorption (0.6%). TAHQ has a chemical structure of

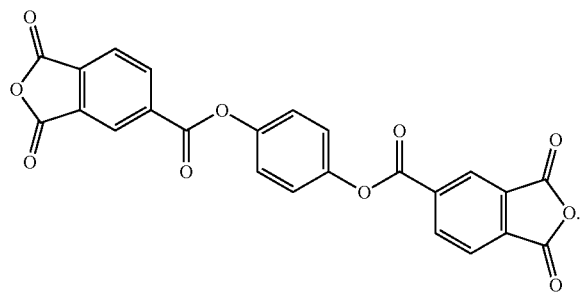 [SMILES: O=C(Oc1ccc(OC(=O)c2ccc3c(c2)C(=O)OC3=O)cc1)c1ccc2c(c1)C(=O)OC2=O]

As shown in the comparison between Example 1 and Comparative Example 1, the polyimide formed from the anhydride compound in Example 1 is preferably applied as 5G board material due to its lower dielectric constant, lower dielectric loss, and lower moisture absorption.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. An anhydride compound, having a chemical structure of

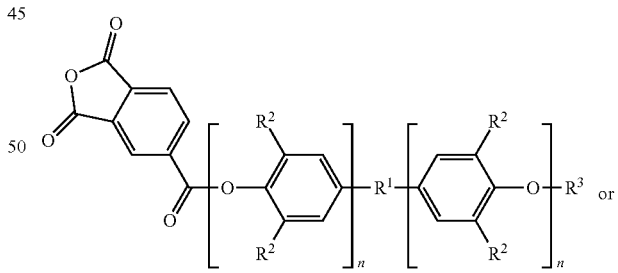

or

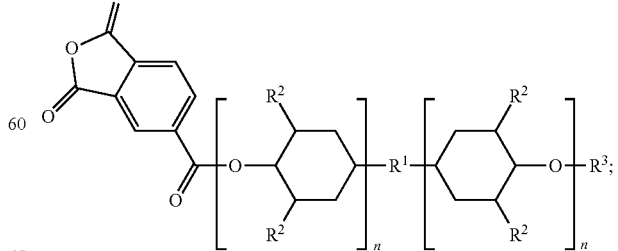

wherein R¹ is

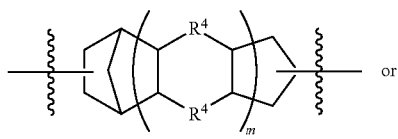 or

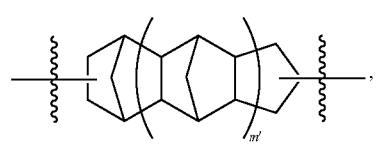, each of R⁴ is independently $C_{1-6}$ alkylene group, m is an integer of 0 to 10, and m' is an integer of 1 to 10;
n is an integer of 1 to 10;
each of R² is independently hydrogen, saturated or unsaturated $C_{1-6}$ hydrocarbon group, $CF_3$, silanol group, silyl group, or $Al(OH)_3$; and R³ is

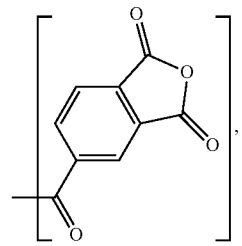

silanol group, silyl group, or $Al(OH)_3$.

2. The anhydride compound as claimed in claim 1, having a chemical structure of

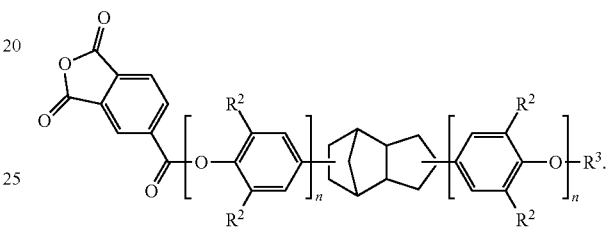

3. The anhydride compound as claimed in claim 1, having a chemical structure of

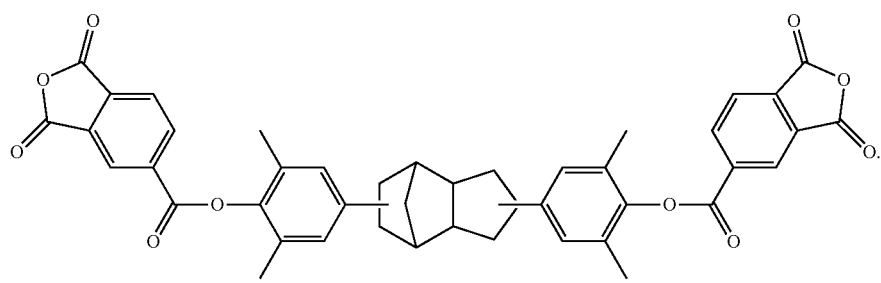

4. The anhydride compound as claimed in claim 1, having a chemical structure of

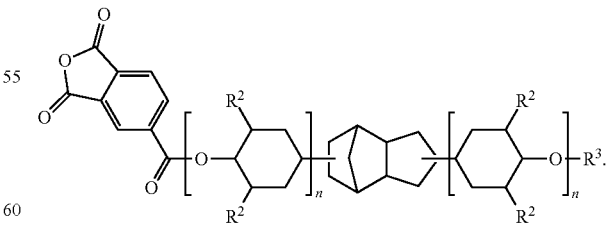

5. The anhydride compound as claimed in claim 1, having a chemical structure of

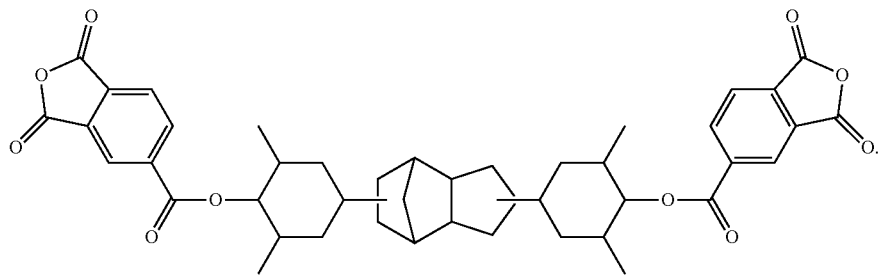

6. A polyimide, being formed by reacting an anhydride compound and a diamine compound;
wherein the anhydride compound has a chemical structure of

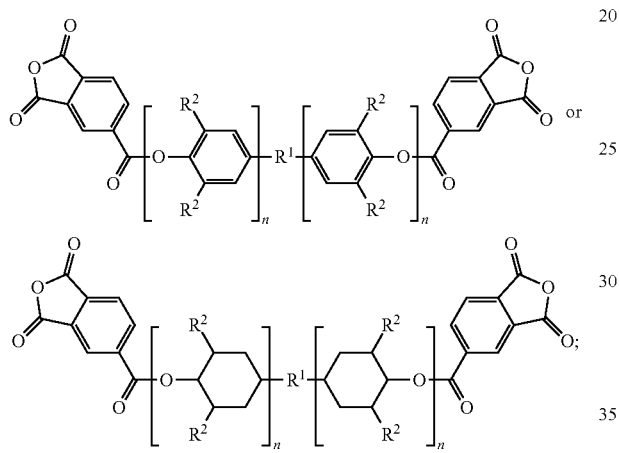

wherein $R^1$ is

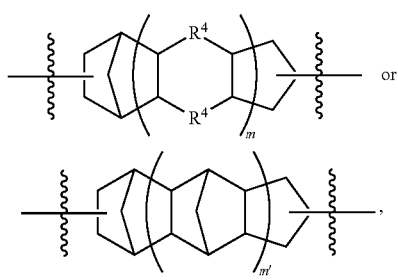

each of $R^4$ is independently $C_{1-6}$ alkylene group, m is an integer of 0 to 10, and m' is an integer of 1 to 10;
n is an integer of 1 to 10; and
each of $R^2$ is independently hydrogen, saturated or unsaturated $C_{1-6}$ hydrocarbon group, $CF_3$, silanol group, silyl group, or $Al(OH)_3$.

7. The polyimide as claimed in claim 6, wherein the diamine compound has a chemical structure of

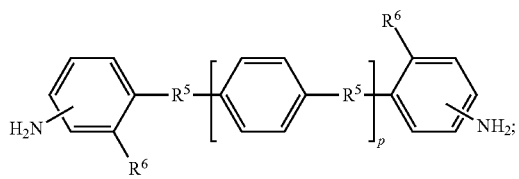

wherein p is an integer of 0 to 5;
each of $R^5$ is independently —O—, —NH—, $C_{1-4}$ alkylene group, —$SO_2$—, —$CF_2$—, —$C_2F_4$—, —(C=O)O—, —(C=O)—, —(C=O)NH—, or —NH(C=O)—; and
each of $R^6$ is independently H, $CH_3$, or $CF_3$.

8. The polyimide as claimed in claim 6, wherein the diamine compound has a chemical structure of

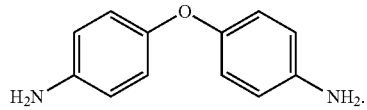

9. A thin film, comprising the polyimide as claimed in claim 6, wherein the thin film has a thickness of 10 µm to 75 µm, and a dielectric constant of 2.5 to 3 at 10 GHz.

* * * * *